United States Patent [19]

Imran

[11] Patent Number: 5,425,364

[45] Date of Patent: Jun. 20, 1995

[54] FLEXIBLE STRIP ASSEMBLY WITHOUT FEEDTHROUGH HOLES AND DEVICE UTILIZING THE SAME

[75] Inventor: Mir A. Imran, Palo Alto, Calif.

[73] Assignee: Cardiac Pathways Corporation, Sunnyvale, Calif.

[21] Appl. No.: 222,902

[22] Filed: Apr. 5, 1994

Related U.S. Application Data

[63] Continuation-in-part of Ser. No. 983,968, Dec. 1, 1992, Pat. No. 5,327,889, and a continuation-in-part of Ser. No. 127,699, Sep. 28, 1993, which is a continuation-in-part of Ser. No. 919,198, Jul. 24, 1992, Pat. No. 5,279,299, which is a continuation-in-part of Ser. No. 656,764, Feb. 15, 1991, Pat. No. 5,156,151.

[51] Int. Cl.$^6$ .................... A61B 5/04; A61N 1/05
[52] U.S. Cl. .................... 128/642; 607/119; 607/122
[58] Field of Search ............... 128/642; 607/115, 116, 607/119, 122, 123, 125–128

[56] References Cited

U.S. PATENT DOCUMENTS

| | | | |
|---|---|---|---|
| 4,461,304 | 7/1984 | Kuperstein | 128/642 |
| 4,890,623 | 1/1990 | Cook et al. | 607/122 X |
| 4,903,702 | 2/1990 | Putz | 128/642 |

FOREIGN PATENT DOCUMENTS 8707825 12/1987 WIPO .................... 607/116

OTHER PUBLICATIONS

Merres et al. "Photolithographic Fabrication and Physiological Performance of Micro electrode Arrays for Neural Stimulation" IEEE Transactions on Biomedical Engineering, vol. BME-25 No. 6, Nov. 1978, 128/642.

*Primary Examiner*—Lee S. Cohen
*Assistant Examiner*—Jeffrey R. Jastrzab
*Attorney, Agent, or Firm*—Flehr, Hohbach, Test, Albritton & Herbert

[57] ABSTRACT

A flexible elongate strip assembly comprising at least one strip having a length and a plurality of longitudinally spaced-apart electrode structures carried by the strip. Each electrode structure is formed with a layer of an insulating material having substantially planar spaced-apart parallel outer and inner surfaces. Each layer of an insulating material is provided with a layer of a conductive material adhered to the inner surface and an opening extending between the outer and inner surfaces to expose at least a portion of the layer of a conductive material on the outer surface. A plurality of spaced-apart generally parallel traces are carried by the strip and extend longitudinally along the length thereof. Conductive elements are provided for connecting the traces to the layers of a conductive material. The exposed portion of the layer of a conductive material serves as a conductive surface for the electrode structure.

18 Claims, 2 Drawing Sheets

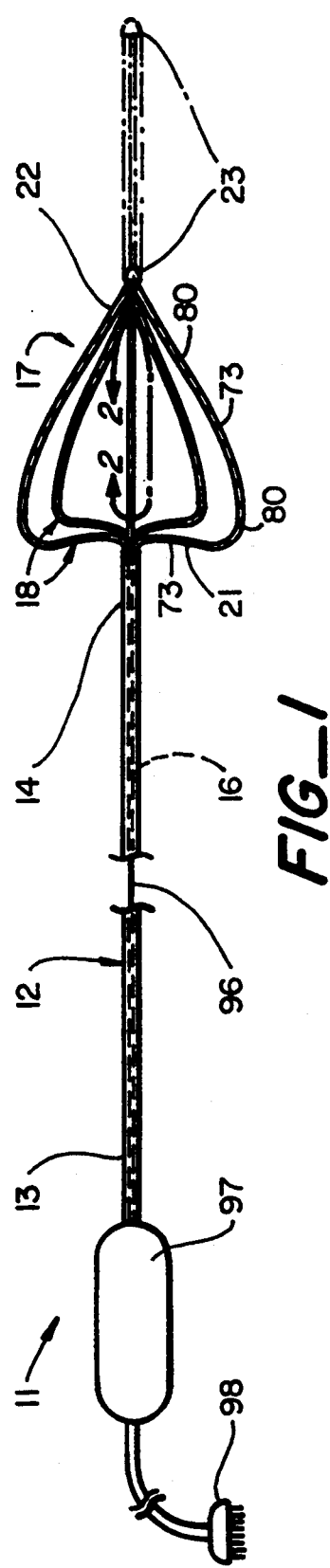
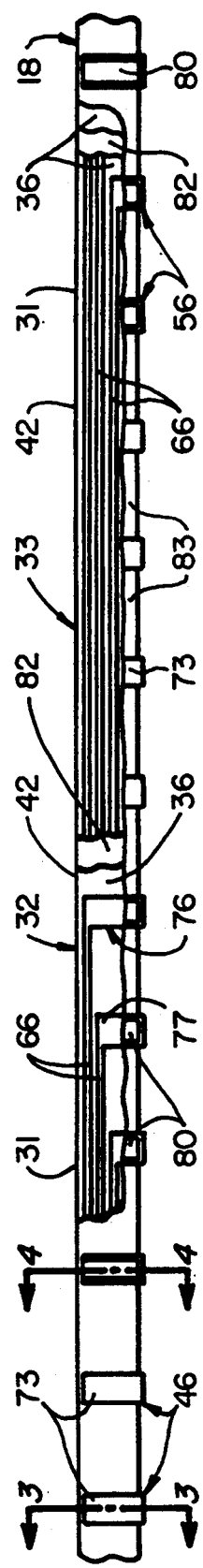
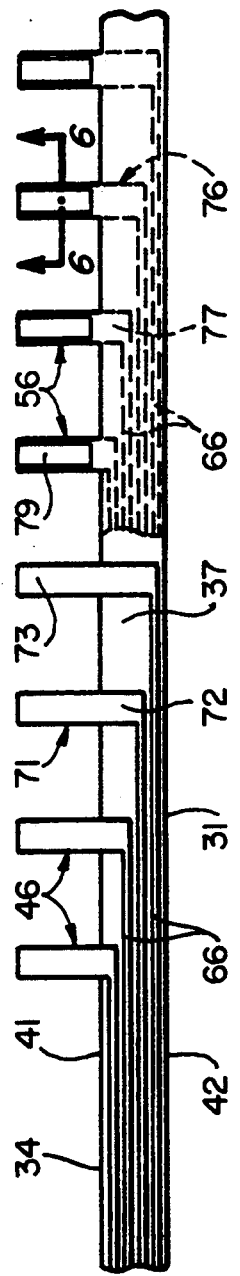

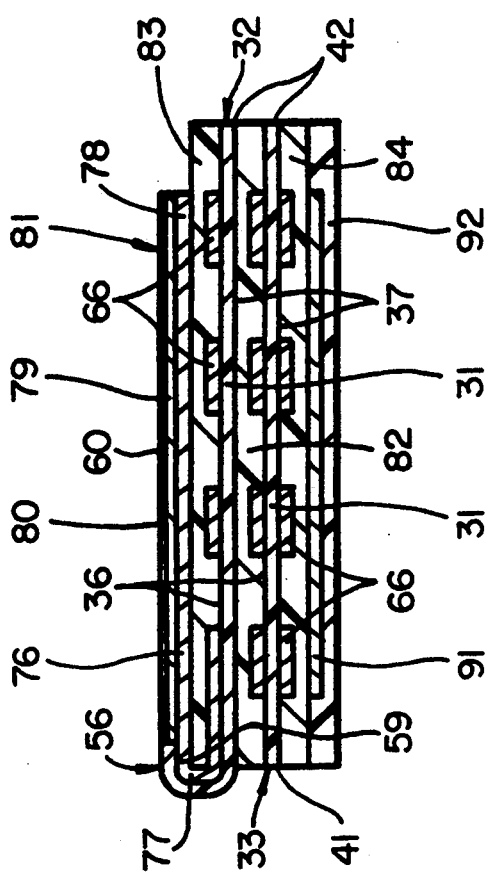
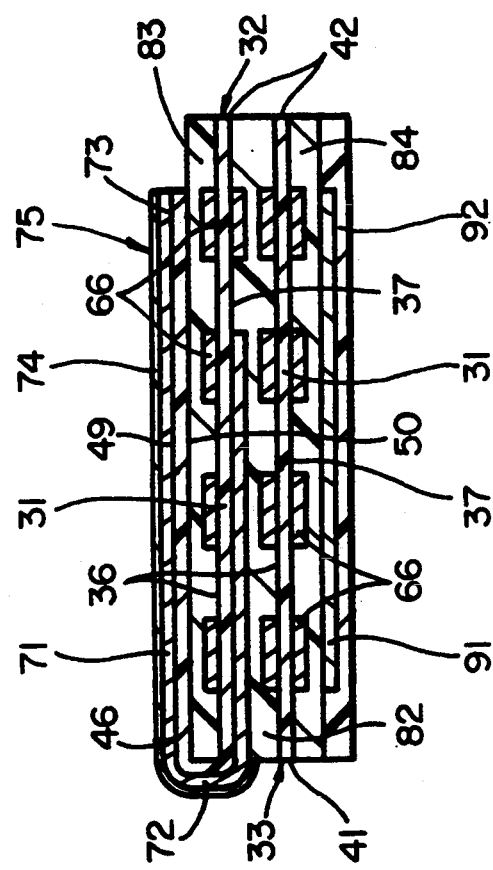
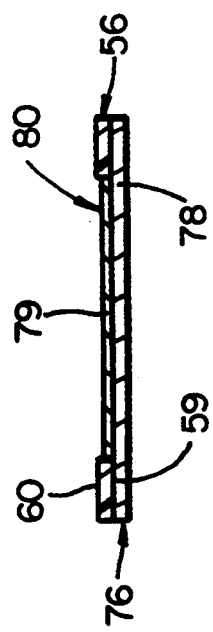

FLEXIBLE STRIP ASSEMBLY WITHOUT FEEDTHROUGH HOLES AND DEVICE UTILIZING THE SAME

CROSS REFERENCE TO RELATED APPLICATIONS

This application is a continuation-in-part of application Ser. No. 07/983,968 filed Dec. 1, 1992, now U.S. Pat. No. 5,327,889 and of application Ser. No. 08/127,699 filed Sep. 28, 1993, which is a continuation-in-part of application Ser. No. 07/919,198 filed Jul. 24, 1992, which is a continuation-in-part of application Ser. No. 07/656,764 filed Feb. 15, 1991, now U.S. Pat. No. 5,156,151.

BACKGROUND OF THE INVENTION

1. Field of the Invention

This invention pertains generally to flexible elongate strip assemblies and, more particularly, to flexible elongate strip assemblies for use with medical devices.

2. Description of the Related Art It has been found that the spatial requirements of feedthrough holes limits the number of traces and hence electrodes which can be carried by a layer of a multilayer strip assembly. Because of the foregoing, there is a need for a new and improved flexible elongate strip assembly which overcomes the above named disadvantages and can be used with a medical device.

OBJECTS OF THE INVENTION

In general, it is an object of the present invention to provide a flexible elongate strip assembly which does not utilize feedthrough holes.

Another object of the invention is to provide a flexible elongate strip assembly of the above character which permits an increased number of conductive traces and electrodes to be carried by a layer thereof.

Additional objects and features of the invention will appear from the following description from which the preferred embodiments are set forth in detail in conjunction with the accompanying drawings.

BRIEF DESCRIPTION OF THE DRAWINGS

FIG. 1 is a side elevational view of a flexible elongate device incorporating the flexible strip assembly of the present invention.

FIG. 2 is an enlarged view, partially cut away, of the flexible strip assembly shown in FIG. 1 taken along the line 2—2 of FIG. 1.

FIG. 3 is a cross-sectional view of the flexible strip assembly of FIG. 2 taken along the line 3—3 of FIG. 2.

FIG. 4 is a cross-sectional view of the flexible strip assembly of FIG. 2 taken along the line 4—4 of FIG. 2.

FIG. 5 is an enlarged bottom plan view of a flex circuit incorporated in the flexible strip assembly of FIG. 2.

FIG. 6 is a cross-sectional view of the flex circuit of FIG. 5 taken along the line 6—6 of FIG. 5.

SUMMARY OF THE INVENTION

In general, the flexible elongate strip assembly of the present invention comprises at least one strip having a length and a plurality of longitudinally spaced-apart electrode structures carried by the strip. Each electrode structure is formed with a layer of an insulating material having substantially planar spaced-apart parallel outer and inner surfaces. Each layer of an insulating material is provided with a layer of a conductive material adhered to the inner surface and an opening extending between the outer and inner surfaces to expose at least a portion of the layer of a conductive material on the outer surface. A plurality of spaced-apart apart generally parallel traces are carried by the strip and extend longitudinally along the length thereof. Conductive means are provided for connecting the traces to the layers of a conductive material. The exposed portion of the layer of a conductive material serves as a conductive surface for the electrode structure.

DETAILED DESCRIPTION

More in particular, a flexible elongate medical device of the present invention can be in the form of a catheter 11 of the type disclosed in U.S. Pat. No. 5,156,151 and copending application Ser. No. 08/044,255 filed Apr. 7, 1993 for mapping the wall of a chamber of the heart having blood therein. As disclosed therein and as illustrated in FIG. 1, endocardial mapping catheter 11 includes a flexible elongate tubular member or shaft 12 which is formed of a suitable material such as plastic and is circular in cross section. Shaft 12 has a proximal extremity 13 adapted to be disposed outside of a human body to permit access to and operation of catheter 11 and a distal extremity 14 adapted to be inserted into the body for performing an operation in the body. At least one lumen 16 extends from proximal extremity 13 to distal extremity 14 of the shaft.

A flexible means in the form of basket assembly 17 is carried by distal extremity 14 and is moveable between a first or contracted position, shown in dotted lines in FIG. 1, and a second or expanded position, shown in solid lines in FIG. 1. Basket assembly 17 is provided with a plurality of longitudinally extending flexible elongate strip assemblies or arms 18 which have an outwardly bowed shaped memory for expanding the basket assembly into engagement with the wall of the heart. Arms 18 have proximal extremities or end portions 21 which are joined to distal extremity 14 of shaft 12 and distal extremities or end portions 22 which are joined at tip 23 of basket assembly 17. When the basket assembly is expanded as illustrated in FIG. 1, arms 18 are circumferentially and symmetrically spaced-apart. A plurality of longitudinally spaced-apart electrodes are supported and carried by each arm 18 for engaging the heart wall.

Each arm 18 is multilayered and includes at least one elongate layer of an insulating material and, as shown in FIGS. 2 through 5, has first or outer and second or inner base layers 31 which form part of outer and inner flex circuits 32 and 33. Layers 31 are made from an insulating plastic material or substrate such as Kapton and have a length, width and thickness. The width, which ranges from approximately 0.025 to 0.050 inch and is preferably 0.04 inch, is greater than the thickness, which ranges from approximately 0.0005 to 0.0100 inch. Layers 31 further include proximal end portions 34 and opposite outer and inner substantially planar spaced-apart parallel surfaces 36 and 37 and opposite first and second substantially planar spaced-apart parallel side wall surfaces 41 and 42 which adjoin surfaces 36 and 37.

At least one of base layers 31 of each arm 18 is formed with a plurality of tab portions which extend generally at substantially right angles from at least one of the side surfaces thereof and are longitudinally spaced apart along the length of the base layers. More specifically, as shown in the drawings, a plurality of four first tab portions 46 are formed integral with each layer 31 and extend at substantially right angles from first side surface 41. Tab portions 46 have opposite first and second surfaces 49 and 50. A plurality of second tab portions 56, similar to tab portions 46 but farther from proximal end portion 34 of the base layer than tab portions 46, are also formed integral with each layer 31 and have opposite first and second surfaces 59 and 60 which are oppositely aligned with first and second surfaces 49 and 50 of first tab portions 46.

A plurality of spaced-apart generally parallel traces 66 of a conductive material are disposed on at least one of surfaces 36 and 37 of each layer 31 to further comprise flex circuits 32 and 33. In the embodiment illustrated in the drawings, four traces 66 formed from any suitable material such as copper are spaced transversely across each of surfaces 36 and 37 and have a minimum width ranging from approximately 0.0010 to 0.0035 inch and a thickness ranging from approximately 0.00035 inch for one-quarter ounce copper to approximately 0.00070 inch for one-half ounce copper. These traces are adhered on the surfaces by any suitable means such as sputter deposition and extend from proximal end portion 34 of the base layer longitudinally along the length of each of the surfaces. The four traces on inner surface 37 of each layer 31 extend to first tab portions 46, with the trace closest first side surface 41 extending to the first tab portion nearest proximal end portion 34 and the second, third and fourth traces across inner surface 37 extending sequentially to the next three first tab portions, respectively (see FIG. 5). Similarly, the four traces 66 on outer surface 36 of each layer 31 extend to the second tab portions 56, the trace closest first side surface 41 extending to the second tab portion closest to proximal end portion 34 and the second, third and fourth traces across outer surface 36 extending sequentially to the next three second tab portions, respectively.

A conductive strip 71 made of any suitable material such as copper extends from the end of each trace 66 on inner surface 37 transversely across each layer 31 and the length of the related tab portion 46 on first surface 49 thereof. Strips 71 are formed on these surfaces by sputter deposition or any other suitable means and have a thickness ranging from approximately 0.00035 inch for one-quarter ounce copper to approximately 0.00070 inch for one-half ounce copper. Strips 71 have proximal portions 72 which extend from the respective trace 66 and distal portions 73 which extend from said proximal portions along the length of first surface 49. Distal portions 73 serve as four of the electrodes of the flex circuit 32 or 33 and proximal portions 72 are included within the conductive means or elements of the present invention which electrically connect distal portions or electrodes 73 to traces 66 on inner surface 37. Electrodes 73 are plated with a thin layer of nickel flash (not shown), over which a layer of gold 74 ranging in thickness from 0.00005 to 0.00020 inch is plated. Strips 71, electrodes 73 and gold 74 are included within an electrode structure 75 of the present invention.

A set of conductive strips 76 similar to strips 71 extend from the end of traces 66 on outer surface 36 transversely across layer 31 and the length of first surfaces 59 of tab portions 56. Strips 76 each have a proximal portion 77 which extends from the respective trace 66 and a distal portion 78 which extend from the proximal portion along the length of the respective tab portion 56. A portion of each second surface 60 opposite the portion of first surface 59 on which the distal portion 78 of conductive strip 76 is formed is etched or otherwise removed so as to expose the underside of distal portion 78 on second surface 60 of tab portion 56 (see FIG. 6). A thin layer of nickel flash (not shown) is plated over the underside of strip distal portion 78 and a layer of a suitable conductive material such as gold 79, having a thickness generally equal to that of gold 74, is plated over second surface 60 and the nickel flash so as to form a conductive pad or electrode 80 on second surface 60. Electrodes 80 serve as the other four electrodes of flex circuit 32 or 33 and proximal end portions 77 of conductive strips 76 are included within the conductive means or elements of the present invention which electrically connect electrodes 80 to traces 66 on outer surface 36. Strips 76, electrodes 80 and gold 79 are included within an electrode structure 81 of the present invention.

In the assembly of each arm 18, outer flex circuit 32 is stacked on top of inner flex circuit 33. Tab portions 46 and 56 of outer flex circuit 32 are longitudinally spaced-apart on arm 18 from tab portions 46 and 56 of inner flex circuit 33. More specifically and as shown in FIG. 2, the tab portions of outer flex circuit 32 are closer to proximal end portion 21 of the arm and the tab portions of inner flex circuit 33 are spaced longitudinally beyond the tab portions of flex circuit 32 so as to be closer to distal end portion 22 of the arm. Inner surface 37 of the outer flex circuit faces toward outer surface 36 of the inner flex circuit but is separated therefrom by an insulating coating or layer 82 made from a suitable material such as polyimide so as to preclude electrical short circuits between the traces of flex circuits 32 and 33. Additional insulating coatings or layers 83 and 84 are disposed respectively over outer surface 36 of outer flex circuit 32 and inner surface 37 of inner flex circuit 33. Insulating layers 82, 83 and 84 sealably adhere to flex circuits 32 and 33 and thereby also serve to preclude body or other fluids from contacting traces 66 and possibly disrupting the electrical signals carried thereby. As so described, the insulating layer 82 of inner flex circuit 33 is adhered to inner surface 37 of layer 31 of outer flex circuit 32.

Tab portions 46 of outer flex circuit 32 extend between outer insulating layer 83 and middle insulating layer 82 and tab portions 46 of inner flex circuit 33 extend between middle insulating layer 82 and inner insulating layer 84. Tab portions 46 are longitudinally sized and foldable so as to permit electrodes 73 thereon to overlie the outer surface of insulating layer 83 and surfaces 36 of flex circuits 32 and 33. Second surfaces 50 of tab portions 46 are bonded or otherwise suitably adhered to the outer surface of insulating layer 83 and, as illustrated in FIG. 3, first surfaces 49 become outer facing surfaces of arm 18 for carrying electrodes 73. Proximal portions 72 of conductive strips 71 extend from inner surfaces 37 around the outside of tab portions 46 and first side surface 41 of flex circuits 32 and/or first side surface 41 of flex circuit 33 to electrically connect traces 66 on inner surfaces 37 to at least some of the electrodes, and as shown in the drawing eight electrodes 73, overlying the outer surfaces of insulating layer 83 and flex circuits 32 and 33.

Tab portions 56 are similarly configured on arms 18, the tab portions 56 of outer flex circuit 32 extending between outer and middle insulating layers 83 and 82 and the tab portions 56 of inner flex circuit 33 extending between middle and inner insulating layers 82 and 84.

Tab portions 56 are longitudinally sized and foldable so as to permit electrodes 80 on second surface 60 thereof to overlie the outer surfaces of outer insulating layer 83 and flex circuits 32 and 33. In this manner, second surfaces 60 become outer facing surfaces of arm 18 for carrying electrodes 80. First surfaces 59 and conductive strips 76 thereon are adhered to the outer surface of insulating layer 83, as shown in FIG. 4, and proximal portions 77 extend around the inside of tab portions 56 and insulating layer 83 to electrically connect traces 66 on outer surfaces 36 of layers 31 to at least some of the electrodes, and as shown in the drawing eight electrodes 80, overlying the outer surfaces of insulating layer 83 and flex circuits 32 and 33.

In the assembly of arm 18 illustrated in the drawings, four electrodes 73 and four electrodes 80 of outer flex circuit 32 are the first and second set of four electrodes on the arm. The four electrodes 73 of inner flex circuit 33 sequentially follow the eight electrodes of flex circuit 32 and the four electrodes 80 of flex circuit 33 are the last four electrodes spaced longitudinally along the arm. It should be appreciated that flex circuits having more than eight electrodes, that is more than four traces provided on each side thereof, and arms formed with more than two flex circuits are within the scope of the present invention.

Basket assembly 17 has an outwardly bowed shaped memory which urges the basket assembly toward its expanded position. In this regard, arms 18 are each provided with a metal strip 91 which is secured to inner insulating layer 84 by any suitable means such as an elongate strip 92 made of any suitable material such as plastic.

Lead means which include wire 96 extend through lumen 16 from distal extremity 14 to proximal extremity 13 of shaft 12 and are connected to traces 66 on proximal end portions 34 of layers 31 by any suitable means such as that disclosed in copending application Ser. No. 08/127,699, filed Sep. 28, 1993. A handle 97 is joined to proximal extremity 13 of shaft 12 and wire 96 carried thereby and carries a connector 98 for permitting electrical connections to wire 96, traces 66 and electrodes 73 and 80.

From the foregoing, it can be seen that a new and improved flexible elongate device having a flexible elongate strip assembly which does not utilize feedthrough holes or vias has been provided. Tab portions 46 and 56 and the conductive strips carried thereby permit an electrical connection between the conductive traces on the flex circuits and the electrodes disposed on the outer surface of the arm without the need of feedthrough holes or vias. The flexible elongate strip assembly so provided permits an increased number of conductive traces and electrodes to be carried by a layer thereof.

What is claimed is:

1. A flexible elongate strip assembly for use in a medical device comprising at least one strip having a length, a plurality of longitudinally spaced-apart electrode structures carried by the strip, each electrode structure being formed with a layer of an insulating material having substantially planar spaced-apart parallel outer and inner surfaces and opposite spaced-apart side wall surfaces adjoining the outer and inner surfaces and a layer of a conductive material overlying the outer surface, a plurality of spaced-apart traces carried by the strip and extending longitudinally along the length thereof and conductive means extending from the traces around a side wall surface for connecting the traces to at least some of the layers of conductive material whereby each layer of a conductive material serves as a conductive surface for an electrode structure.

2. A strip assembly as in claim 1 wherein the strip has opposite substantially planar spaced-apart parallel outer and inner surfaces and wherein said traces are adhered to the inner surface of the strip.

3. A strip assembly as in claim 2 together with a plurality of spaced-apart additional traces adhered to the outer surface of the strip and extending longitudinally along the length thereof and additional conductive means extending from the additional traces around a side wall surface for connecting the additional traces to at least some of the layers of conductive material.

4. A strip assembly as in claim 1 wherein each layer of conductive material is adhered to the outer surface of the layer of insulating material.

5. A strip assembly as in claim 1 wherein the strip has opposite substantially planar spaced-apart parallel outer and inner surfaces and wherein said traces are adhered to the outer surface of the strip.

6. A flexible elongate strip assembly for use in a medical device comprising at least one layer having a length, width and thickness in which the width is greater than the thickness, the at least one layer being formed of an insulating material and having substantially planar spaced-apart parallel outer and inner surfaces and opposite spaced-apart side wall surfaces adjoining the outer and inner surfaces, a plurality of longitudinally spaced-apart electrodes overlying the outer surface, a plurality of spaced-apart traces of a conductive material adhered to the inner surface and extending longitudinally of the inner surface along the length of the at least one layer, and conductive means extending from the inner surface around a side wall surface to connect the traces to at least some of the electrodes overlying the outer surface.

7. A strip assembly as in claim 6 wherein the at least one layer is provided with a plurality of tab portions extending at angles from at least one of the side wall surfaces and spaced apart longitudinally along the length of the same and wherein the conductive means extend from the traces along at least a portion of the tab portions, the tab portions being foldable so as to permit the conductive means to be electrically connected to at least some of the electrodes.

8. A strip assembly as in claim 7 wherein the tab portions are folded so as to overlie the outer surface and wherein the tab portions have outer facing surfaces when so folded on which at least some of the electrodes are disposed.

9. A strip assembly as in claim 7 wherein the tab portions extend at substantially right angles from at least one of the side wall surfaces.

10. A strip assembly as in claim 6 together with spaced-apart additional traces of a conductive material adhered to the outer surface and extending longitudinally of the outer surface along the length of the at least one layer, the additional traces electrically connected to at least some of the electrodes overlying the outer surface.

11. A strip assembly as in claim 6 together with an additional layer of insulating material underlying the inner surface of the at least one layer, the additional layer having a length, width and thickness in which the width is greater than the thickness, the additional layer having opposite outer and inner substantially planar spaced-apart parallel surfaces, a plurality of spaced-apart additional traces of a conductive material adhered to at least one of the outer and inner surfaces of the additional layer and extending longitudinally of said at least one surface of the additional layer along the length of the additional layer, and additional conductive means extending from said at least one surface of the additional layer around at least one of the side wall surfaces of the at least one layer to connect the additional traces to at least some of the electrodes overlying the outer surface of the at least one layer.

12. A flexible elongate device comprising a flexible elongate member having proximal and distal extremities, a plurality of spaced-apart electrodes, flexible means secured to the distal extremity of the flexible elongate member for supporting said electrodes for movement between first and second positions, the flexible means comprising at least one flexible elongate strip assembly which includes at least one layer having a length, width and thickness in which the width is greater than the thickness, the at least one layer being formed of an insulating material, the at least one layer having opposite outer and inner substantially planar spaced-apart parallel surfaces and opposite spaced-apart side wall surfaces adjoining the outer and inner surfaces, the electrodes overlying the outer surface, a plurality of spaced-apart traces of a conductive material adhered to the inner surface and extending longitudinally of the inner surface along the length of the at least one layer, and conductive means extending from the inner surface around a side wall surface to connect the traces to at least some of the electrodes overlying the outer surface.

13. A device as in claim 12 together with leads connected to the traces and extending from the distal extremity to the proximal extremity of the flexible elongate member.

14. A device as in claim 13 together with a handle coupled to the proximal extremity of the flexible elongate member and the leads.

15. A flexible elongate strip assembly for use in a medical device comprising at least one layer having a length, width and thickness in which the width is greater than the thickness, the layer being formed of an insulating material and having substantially planar spaced-apart parallel outer and inner surfaces and opposite spaced-apart side wall surfaces adjoining the outer and inner surfaces, at least one electrode overlying the outer surface, at least one trace of a conductive material adhered to the inner surface and extending longitudinally of the inner surface along the length of the layer, and conductive means extending from the inner surface around a side wall surface to connect the trace to the electrode overlying the outer surface.

16. A strip assembly as in claim 15 wherein the layer is provided with at least one tab portion extending at an angle from a side wall surface and wherein the conductive means extends from the trace along at least a portion of the tab portion, the tab portion being foldable so as to permit the conductive means to be electrically connected to the electrode.

17. A strip assembly as in claim 16 wherein the tab portion is folded so as to overlying the outer surface and wherein the tab portion has an outer facing surface when so folded on which the electrode is disposed.

18. A strip assembly as in claim 15 together with an additional electrode overlying the outer surface and an additional trace of a conductive material adhered to the outer surface and extending longitudinally of the outer surface along the length of the layer, the additional trace electrically connected to the additional electrode overlying the outer surface.

* * * * *